(12) United States Patent
Drewry et al.

(10) Patent No.: US 7,837,714 B2
(45) Date of Patent: Nov. 23, 2010

(54) METHODS AND DEVICES FOR THE INTERCONNECTION OF BONE ATTACHMENT DEVICES

(75) Inventors: Troy D. Drewry, Memphis, TN (US); William Barry Null, Olive Branch, MS (US); Marc T. Paul, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 641 days.

(21) Appl. No.: 11/401,732

(22) Filed: Apr. 10, 2006

(65) Prior Publication Data

US 2007/0270808 A1    Nov. 22, 2007

(51) Int. Cl.
*A61B 17/70* (2006.01)
(52) U.S. Cl. .................................................. 606/250
(58) Field of Classification Search ................ 606/250, 606/251, 252, 253, 270
See application file for complete search history.

(56) References Cited

U.S. PATENT DOCUMENTS

| | | | | |
|---|---|---|---|---|
| 4,957,495 | A | * | 9/1990 | Kluger ........................ 606/58 |
| 5,084,049 | A | | 1/1992 | Asher et al. |
| 5,133,716 | A | | 7/1992 | Plaza |
| 5,261,907 | A | * | 11/1993 | Vignaud et al. ............... 606/60 |
| 5,261,913 | A | | 11/1993 | Marnay |
| 5,522,816 | A | | 6/1996 | Dinello et al. |
| 5,607,425 | A | | 3/1997 | Rogozinski |
| 5,624,442 | A | | 4/1997 | Mellinger et al. |
| 5,630,816 | A | | 5/1997 | Kambin |
| 5,667,507 | A | | 9/1997 | Corin et al. |
| 5,707,372 | A | | 1/1998 | Errico et al. |
| 5,709,684 | A | | 1/1998 | Errico et al. |
| 5,752,955 | A | | 5/1998 | Errico |
| 5,885,284 | A | * | 3/1999 | Errico et al. ................. 606/252 |
| 5,980,521 | A | | 11/1999 | Montague et al. |
| 5,980,523 | A | | 11/1999 | Jackson |
| 6,139,548 | A | | 10/2000 | Errico |
| 6,217,578 | B1 | | 4/2001 | Crozet et al. |
| 6,238,396 | B1 | | 5/2001 | Lombardo |
| 6,261,288 | B1 | | 7/2001 | Jackson |
| 6,264,658 | B1 | | 7/2001 | Lee et al. |
| 6,283,967 | B1 | | 9/2001 | Troxell et al. |
| 6,432,108 | B1 | | 8/2002 | Burgess et al. |
| 6,592,585 | B2 | * | 7/2003 | Choi et al. ................... 606/252 |
| 6,699,248 | B2 | | 3/2004 | Jackson |
| 6,736,817 | B2 | | 5/2004 | Troxell et al. |
| 6,761,721 | B2 | | 7/2004 | Burgess et al. |
| 6,872,208 | B1 | | 3/2005 | McBride et al. |

(Continued)

FOREIGN PATENT DOCUMENTS

AU    B-16372/92    11/1992

(Continued)

*Primary Examiner*—Eduardo C Robert
*Assistant Examiner*—Elana B Fisher

(57) ABSTRACT

A pair of bone attachment devices and a crosslink device for a spinal fixation system or other implant arrangement is provided that extends between and engages the bone attachment devices with engaging members. The bone attachment devices include a receiver portion and the crosslink device includes a pair of elongated bridging members each having a pivotally attached connector for connecting to the bone attachment devices at various planar elevations. An interconnection device situated between the connectors receives the members and allows translational and rotational adjustment of the members relative to one another.

16 Claims, 7 Drawing Sheets

U.S. PATENT DOCUMENTS

| | | |
|---|---|---|
| 6,877,241 B2 | 4/2005 | Barr et al. |
| 6,916,319 B2 | 7/2005 | Munting |
| 2002/0007183 A1 | 1/2002 | Lee et al. |
| 2003/0114852 A1* | 6/2003 | Biedermann et al. .......... 606/61 |
| 2003/0114853 A1 | 6/2003 | Burgess et al. |
| 2003/0153914 A1 | 8/2003 | Oribe et al. |
| 2004/0049188 A1 | 3/2004 | Slivka et al. |
| 2004/0116928 A1* | 6/2004 | Young et al. ................. 606/61 |
| 2004/0133203 A1 | 7/2004 | Young et al. |
| 2004/0176765 A1 | 9/2004 | Troxell et al. |
| 2005/0090821 A1 | 4/2005 | Berrevoets et al. |
| 2005/0101956 A1 | 5/2005 | Simonson |
| 2005/0177152 A1 | 8/2005 | Baynham et al. |
| 2005/0216005 A1 | 9/2005 | Howland |
| 2005/0228326 A1* | 10/2005 | Kalfas et al. ................. 602/19 |
| 2006/0064091 A1 | 3/2006 | Ludwig et al. |
| 2007/0270809 A1 | 11/2007 | Drewry et al. |

FOREIGN PATENT DOCUMENTS

| | | |
|---|---|---|
| EP | 0 514 303 | 11/1992 |
| WO | WO 02/076315 | 10/2002 |
| WO | WO 03/030759 | 4/2003 |

* cited by examiner

METHODS AND DEVICES FOR THE INTERCONNECTION OF BONE ATTACHMENT DEVICES

BACKGROUND

The present invention relates to a prosthetic device and a manner of using the same, and more particularly, but not exclusively, relates to the interconnection of components to assemble an orthopedic construct for treatment of a spinal deformity.

The use of prosthetic implants to address orthopedic injuries and ailments has become commonplace. In this arena, it is often desired to decrease the invasiveness of the procedures, improve implant integrity, and provide more positive patient outcomes. Some of these implants depend on interconnection between various system components. Unfortunately, current interconnection devices can be limiting in certain applications. Thus, there is a need for additional contributions in this area of technology.

SUMMARY

One aspect of the present application is a unique prosthesis. Other aspects include unique methods, systems, devices, instrumentation, and apparatus involving an orthopedic implantable construct.

In one aspect there is a system that includes a pair of bone attachment devices designed to engage or attach to bone or a bony structure. Also included is a crosslink device which is structured to form a rigid mechanical connection between the two bone attachment devices and is capable of spanning a range of distances separating the two bone attachment devices and angular orientations between the two bone attachment devices. The ends of the crosslink device include a pivotal connection device that each engage a respective one of the first and second bone attachment devices with an engaging member.

In a further aspect, there is provided a surgical method that includes affixing a first bone attachment device and a second bone attachment device to a corresponding desired skeletal location such as the spine; angularly and translationally adjusting first and second members of a crosslink device relative to one another; pivotally adjusting connectors at the ends of the first and second members of the cross-link device, and securing the connectors to respective ones of the bone attachment devices.

Still another aspect includes a bone attachment device with a receiver portion, a crosslink device, and an elongate spinal stabilization element such as a rod or plate structured to extend through or about the receiver portion. The crosslink device includes a first member and a second member each having means for pivotally attaching a connector thereto. The crosslink device further includes means for adjusting the translational and rotational position of the first and second members relative to one another. Also included are means for fixing one of the first and second connectors, the elongate element, and the bone attachment device together in a rigid construct.

Yet another embodiment of the present invention includes: attaching two bone attachment devices, each having a receiver portion, to a corresponding desired skeletal location; providing two elongate spinal stabilization elements; and positioning each of the two elongate elements in or on the receiver portion of a different one of the bone attachment devices; spanning distance between the bone attachment devices with a crosslink having an interconnection device for adjustably connecting two bridge members, each bridge member having a connector pivotally attached thereto at an end thereof opposite the interconnection device; changing the translational and rotational position of the two bridge members relative to one another; changing the planar and angular position of each of the members relative to the bone attachment device; and securing the bridge members to a different one of each of the bone attachment devices and fixing the bone attachment devices, the elongate elements, and the crosslink together in a rigid construct.

Further embodiments, forms, features, aspects, benefits, objects, and advantages of the present application shall become apparent from the detailed description and figures provided herewith.

DETAILED DESCRIPTION OF SELECTED EMBODIMENTS

Figure 1:
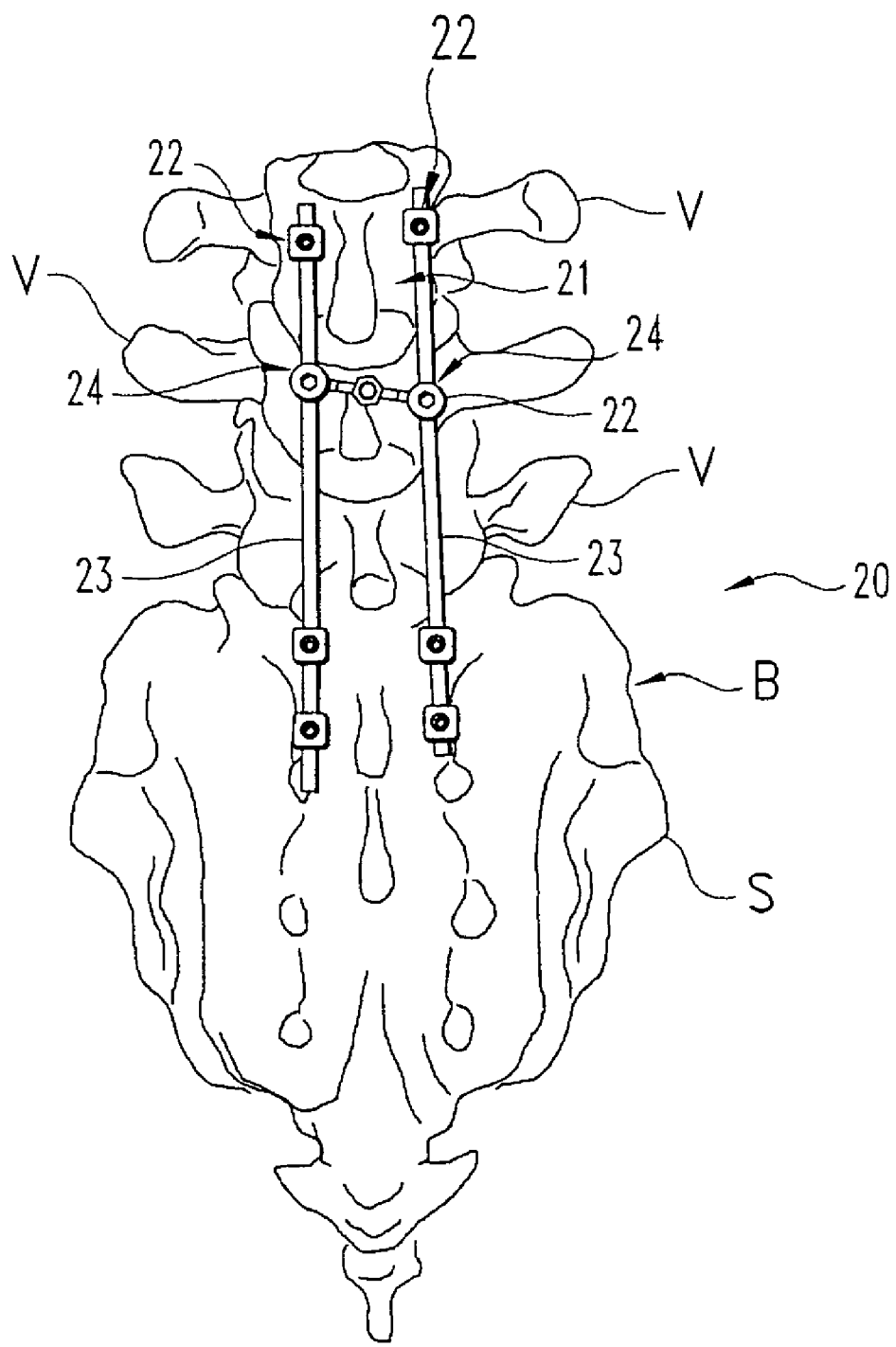
FIG. 1 is a posterior view of a spinal fixation system including a crosslink apparatus relative to the spinal column of a patient.

For the purpose of promoting an understanding of the principles of the invention, reference will now be made to the embodiments illustrated in the drawings and specific language will be used to describe the same. It will nevertheless be understood that no limitation of the scope of the invention is thereby intended. Any alterations and further modifications in the described embodiments, and any further applications of the principles of the invention as described herein are contemplated as would normally occur to one skilled in the art to which the invention relates.

The present invention provides unique orthopedic prosthesis, systems, methods of use and manufacture, devices, instruments, and kits. Incorporated herein by reference in its entirety is U.S. patent application Ser. No. 11/401,822, filed on Apr. 10, 2006, entitled "CROSSLINK INTERCONNECTION OF BONE ATTACHMENT DEVICES".

FIG. 1 illustrates a posterior spinal fixation system 20 of one embodiment located at a desired skeletal location of a patient. More specifically, as depicted in FIG. 1, system 20 is affixed to bones B of the spinal column 21 from a posterior approach. Bones B include the sacrum S and several vertebrae V. System 20 generally includes several bone attachment devices 22 and elongate spinal stabilization elements such as rods 23 structured to selectively interconnect with bone attachment devices 22. In system 20, bone attachment devices 22 are affixed to various locations of the spinal column 21 and interconnected with rods 23. Bone attachment devices 22 may also be interconnected by a crosslink apparatus 24 to provide a stable construct for treating spinal disorders. Posterior fixation system 20 may be used for, but is not limited to, treatment of degenerative spondylolisthesis, fracture, dislocation, scoliosis, kyphosis, spinal tumor, and/or a failed previous fusion.

Figure 2:
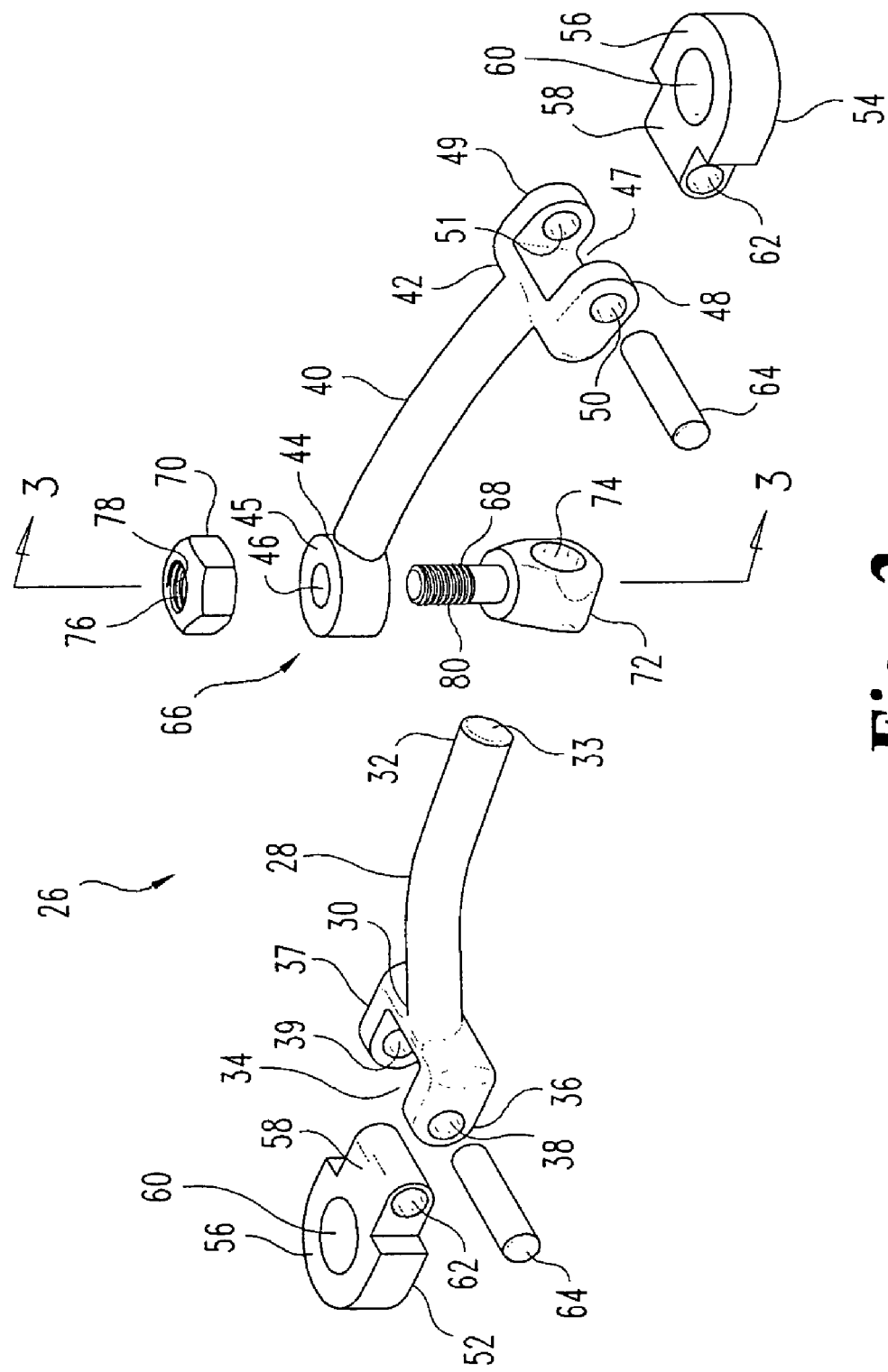
FIG. 2 is an exploded assembly view of a crosslink device of the crosslink apparatus of FIG. 1.

FIG. 2 is an exploded assembly view of a crosslink device 26 of crosslink apparatus 24 in FIG. 1. Crosslink device 26 includes a first bridging member 28 with a first connector 52 and a second bridging member 40 with a second connector 54. First and second bridging members 28, 40 can be engaged to one another at ends thereof opposite the respective connectors 52, 54 with an adjustable linking/interconnection device 66. Cross-link device 26 can extend between and interconnect respective ones of the first and second bone attachment devices 22 through which rods 23 are positioned. Cross-link device 26 can include linking/interconnection device 66 that allows change of the angular orientation between and the length of first and second bridging members 28, 40, providing adjustability in the positioning of cross-link device 26 between attachment devices 22 to avoid anatomical structures along the spine.

Crosslink device 26 includes first elongated bridging member 28 having a first end 30 opposite a second end 32. First end 30 includes a first socket 34 defined by a pair of outwardly extending prongs 36 and 37 including apertures 38 and 39 transversely formed therethrough. Crosslink device 26 further includes second elongate bridging member 40 having a first end 42 opposite a second end 44. First end 42 includes a second socket 47 defined by a pair of outwardly extending prongs 48 and 49 including apertures 50 and 51 formed transversely therethrough. As depicted, bridging members 28 and 40 between respective first ends 30 and 42 and second ends 32 and 44 include an arcuate configuration so that in the operative, implanted position bridging members 28 and 40 are convexly curved away from the spinal column to provide clearance over anatomical structures. In alternative embodiments members 28 and 40 may be more or less arcuate and may even be straight.

First and second sockets 34, 47 are each sized and structured to receive first connector 52 and second connector 54 therein, respectively. Each of first connector 52 and second connector 54 includes a body 56 and a branch 58 extending from body 56 wherein branch 58 is appropriately sized relative to first socket 34 and second socket 47 and is structured for insertion therein. Branch 58 further includes an aperture 62 extending transversely therethrough such that when connectors 52 and 54 are inserted into sockets 34 and 47 respectively, aperture 62 of branch 58 aligns with apertures 38, 39 and 50, 51. When aligned appropriately, a fulcrum 64 shown in the form of pin may be inserted through aperture 38 of prong 36, through aperture 62, and through aperture 39 of prong 37 to pivotally interconnect connector 52 with socket 34. Similarly, when properly aligned, connector 54 may be pivotally interconnected to socket 47 by inserting fulcrum 64 through aperture 50 of prong 48, through aperture 62, and then through aperture 51 of prong 49.

It is contemplated that any of apertures 38, 39, 50, and 51 may include threading therein, such that fulcrum 64 may be in the form of a bolt or screw. Fulcrum 64 can also be press fit, welded or otherwise secured to one or both of the prongs of the respective socket. Fulcrum 64 may also be a standard bolt and nut combination or any other device known to those skilled in the art capable of permitting pivotal movement thereabout. It is also contemplated that the arrangement between the branch and socket could be reversed so that one or both of connectors 52, 54 defines a socket and the respective adjacent end of bridging member 28, 40 defines a branch pivotally coupled in the socket.

Figure 4:
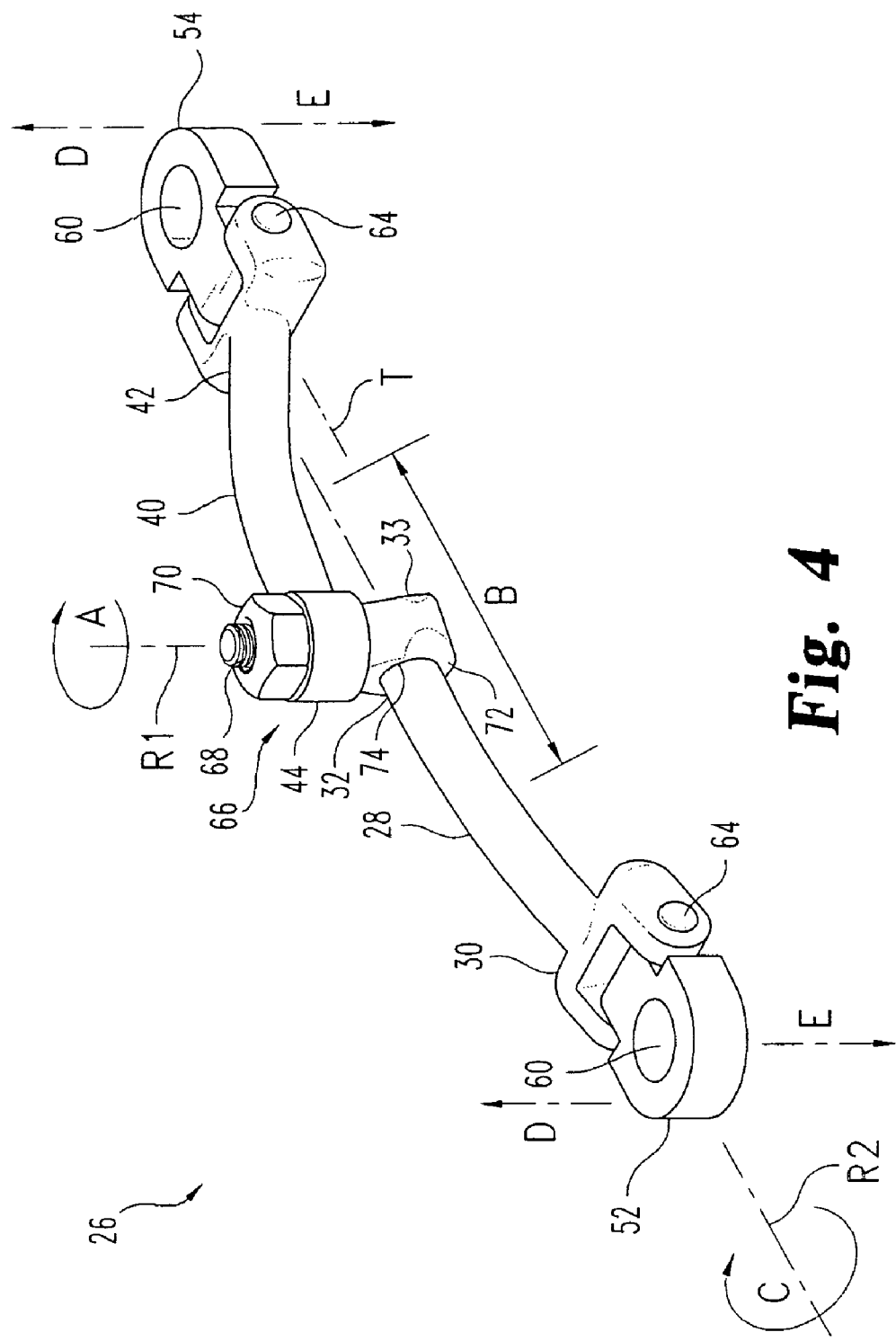
FIG. 4 is a perspective view of the crosslink device in FIG. 2.

Referring to the side plan view of crosslink device 26 in FIG. 4, there is illustrated the directions of pivotal movement of connectors 52 and 54 about fulcrum 64. Connectors 52 and 54 may pivot freely in an upward or downward direction as indicated by respective Directional Arrows D and E. While connectors 52 and 54 are illustrated as being substantially in the same plane, it is intended that their planar relationship will shift when crosslink device 26 is attached to bone attachment devices 22 having different elevational locations within the body and having different angular orientations relative to one another and relative to the connectors 52, 54. The ability to adjust the angular orientation of the ends of bridging members 28, 40 with connectors 52, 54 facilitates attachment of crosslink device 26 between bone attachment devices with an infinite number of relative locations and angular orientations between the bone attachment devices.

In one embodiment, body 56 of connectors 52 and 54 includes an aperture 60 therethrough to facilitate engagement with bone attachment devices 22 of FIG. 1. In alternative embodiments (not shown) body 56 does not an aperture 60 that is completely enclosed. In one such variation, an open collar with a slot is defined by each body 56 of connectors 52 and 54 in lieu of the enclosed aperture 60. In another form, the structures of connectors 52 and 54 have a different means for engaging the respective bone attachment devices 22. Correspondingly, the shape and size of bridging members 28 and 40 can differ from that depicted as desired for a particular application.

For example, the connectors 52, 54 can abut against the ends of the respective receiver portions 90, or may include a cavity to at least partially receive the respective receiver portion 90 therein. It should be further understood that connectors 52, 54 may rotate around the bone attachment device 22 until finally secured thereto with an engaging member. The rotational adjustability of the connectors 52, 54 and thus bridging members 28, 40 with respect to the bone attachment devices further facilitates adjustment in the angular orientation and length of the bridging members 28, 40 relative to one another.

Crosslink device 26 further includes an adjustable linking/interconnection device 66 having a stem 68, a fastener 70, and a sleeve 72 defining a passageway 74. A detailed cross sectional view of interconnection device 66 is provided in FIG. 3 that corresponds to the section line 3-3 presented in FIG. 2. Sleeve 72 is positioned opposite stem 68, which extends away therefrom. Bridging member 40 is structured for rotatable engagement with stem 68 and bridging member 28 is structured for translational and rotatable engagement within passageway 74 of sleeve 72. Second end portion 44 of bridging member 40 includes end portion 45 that defines a passage 46 therethrough.

When assembled together as shown in FIGS. 1 and 3-7, stem 68 of device 66 extends through passage 46. As in the case of aperture 60, passage 46 can alternatively be defined as a fork, slot, shim, collar, or blade (just to name a few possibilities) that receives stem 68 instead of the enclosed structure of passage 46. Referring to FIG. 4, bridging member 40 can be moved through a range of rotational positions about axis R1, as represented by the rotational motion arrow A.

Bridging member 28 includes second end 32 opposite first end 30 that defines an end portion 33 that extends through passageway 74 of sleeve 72, and has a range of translational motion along axis T as represented by range segment B in FIG. 4. Furthermore, passageway 74 and end portion 33 are sized and shaped to facilitate a range of rotational positions about axis R2 relative to passageway 74 and sleeve 72 as represented by rotational motion arrow C in FIG. 4.

Figure 3:
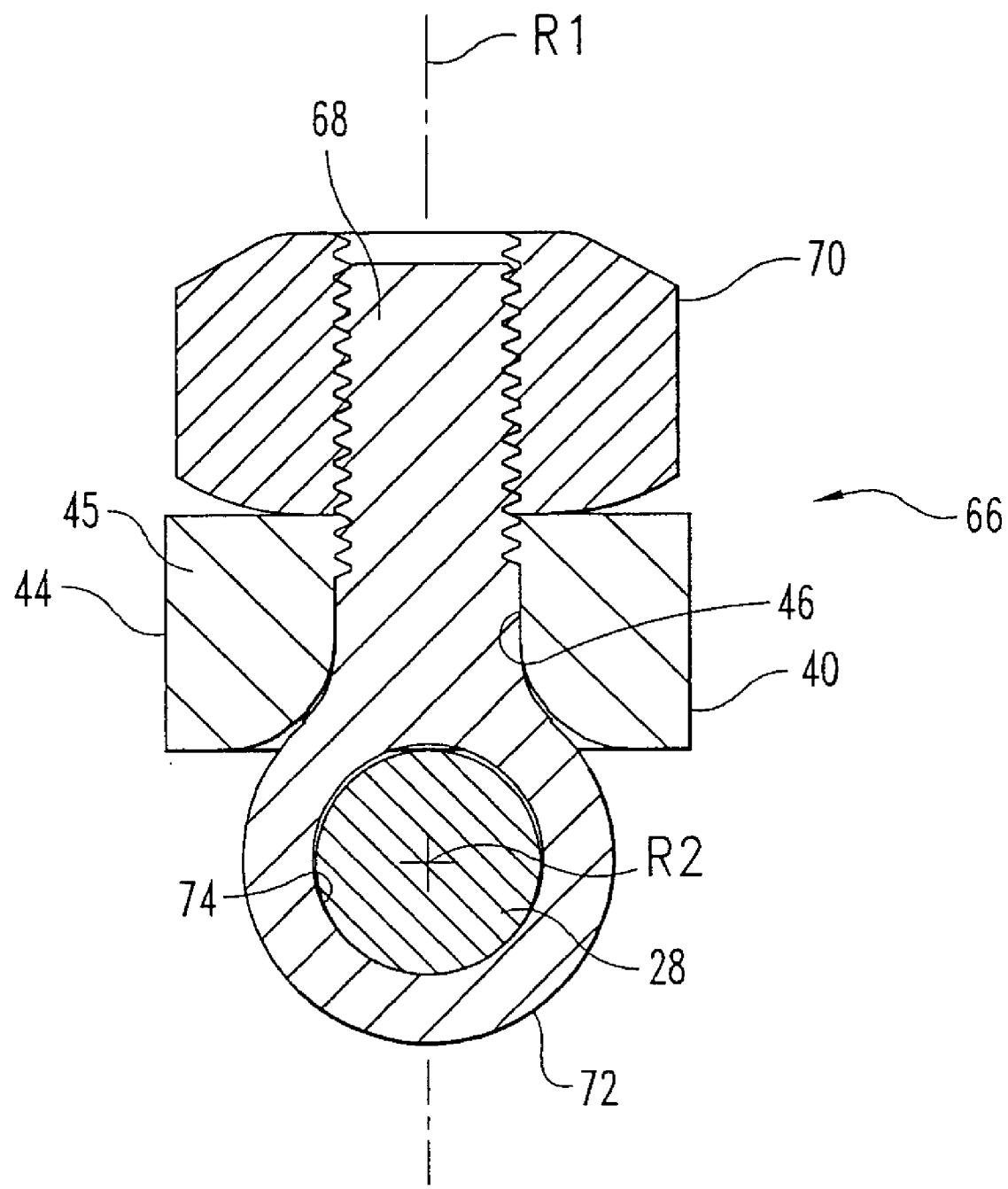
FIG. 3 is a cross sectional view of an interconnection device of the crosslink device shown in FIG. 2 when viewed in direction 3-3 of FIG. 2.

After extending stem 68 through passage 46 and end portion 33 through passageway 74 and determining selected positioning relative to axes R1, R2, and T, fastener 70 including an aperture 76 with internal threading 78 is engaged with threading 80 on stem 68. As fastener 70 is turned, sleeve 72 brings end portion 33 into contact with end portion 45, forming a bearing relationship therebetween that resists movement therebetween. Correspondingly, bridging members 28 and 40 become fixed relative to one another as fastener 70 is tightened on stem 68 to bear against a side of end portion 33 opposite the side in contact with end portion 45. It should be appreciated that before final tightening, refinements can be made in the relative positioning. Once fastener 70 is finally tightened a bridging construct is provided that spans between a pair of bone attachment devices 22 with a selected rotational configuration relative to axes R1 and R2 (and ranges A and C) and a selected translational configuration relative to axis T along range segment B. It should be appreciated that axes R1 and R2 are approximately orthogonal to one another, bridging members 28, 40 can be angularly adjusted relative to one another about axis R1. The angular orientation of connectors 52, 54 relative to another can be adjusted by rotation of bridging member 28 about axis R2. In FIG. 3, axis R1 is parallel to the view plane, but axis R2 is perpendicular thereto, being represented by cross hairs. Translation axis T is parallel to axis R2, as best shown in FIG. 4.

Figure 5:
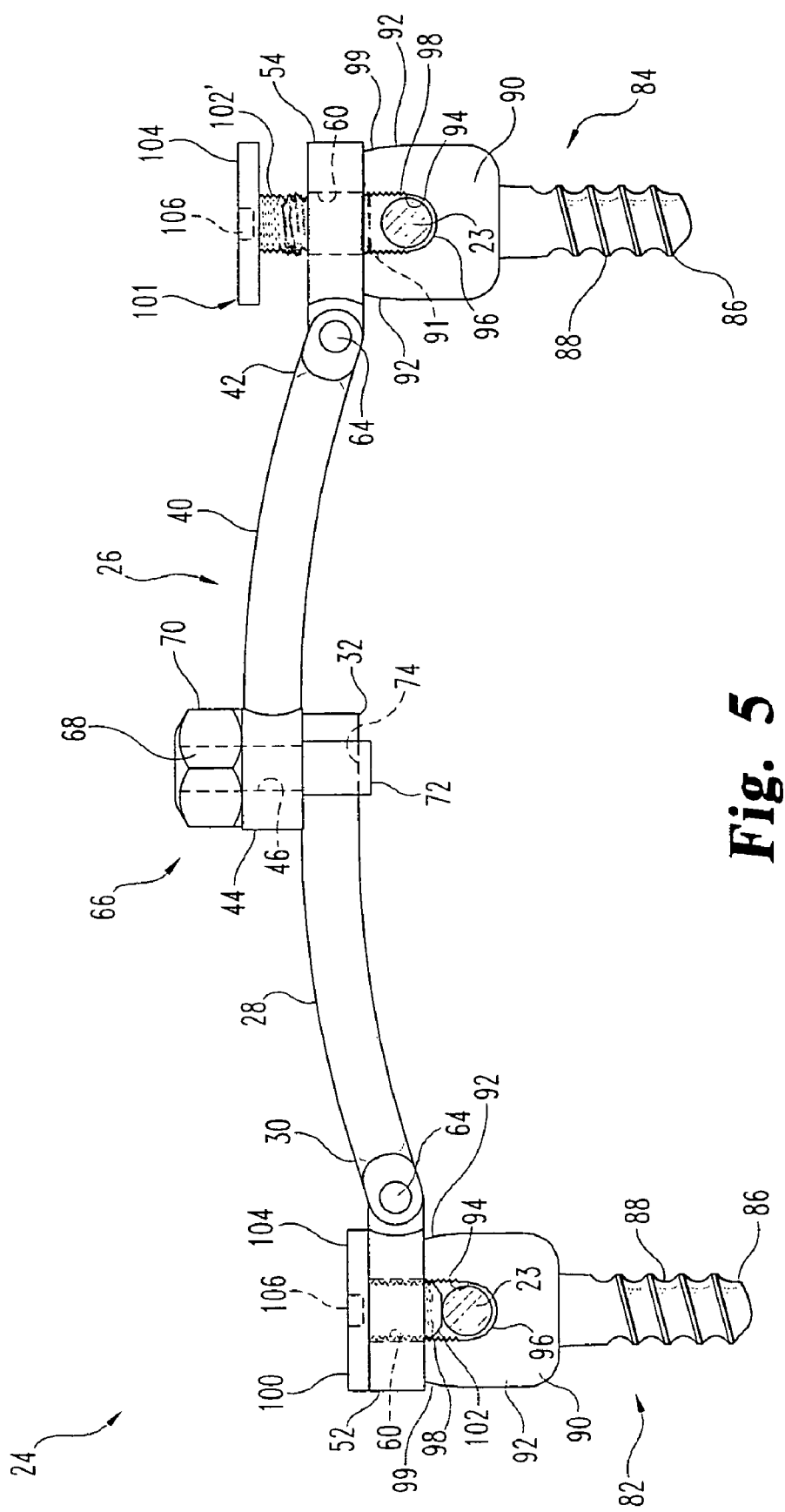
FIG. 5 is a side plan view of the crosslink device relative to spinal implant components of the spinal fixation system of FIG. 1, with some features shown in phantom.

Referring now to FIG. 5, there is shown crosslink apparatus 24 of FIG. 1 with certain hidden features in phantom. Crosslink apparatus 24 includes crosslink device 26 and a pair of bone attachment devices in the form of bone screw 82 and bone screw 84. Bone screws 82 and 84, respectively, can each have an elongated shaft or stem 86 with a helical threaded portion 88. Stem 86 is structured to threadingly engage a passageway prepared in one or more bones or bony structures in a standard manner, and can be provided with cutting flutes or other structure for self-tapping and/or self-drilling capabilities. Stem 86 can also be cannulated to receive a guidewire to facilitate placement and may further include fenestrations or other openings for placement of bone growth material.

Bone screw 82 and bone screw 84 each have a head or a receiver portion 90 defining a receiving channel 94 between upright arms 92. Arms 92 can include an internal threading 98. In alternative embodiments not shown, head 90 includes a receiving channel 94 but does not include threading 98, or may include external threading in addition to or alternatively to threading 98. Receiving channel 94 can form a channel structured to passively secure rod 23 in receiver portion 90 without additional securing means for those embodiments including rod 23. Bottom portion 96 can be concavely curved and form a portion of a circle to receive the rod in form fitting engagement therein. Other embodiments contemplate that the rod is positioned against a head of a bone screw, or against a cap or crown adjacent a head of a bone screw in receiver portion 90.

In one form bone screw 82 and bone screw 84 are made of medical grade stainless steel but other embodiments may be composed of, but are not limited to, titanium, a titanium alloy or other metallic alloy, and/or a nonmetallic composition. Bone attachment devices 22 may be, but are not limited to, multi-axial, poly-axial, uni-axial, uni-planar bone screws where stem 86 and receiver portion 90 are movable relative to one another. In one movable form, stem 86 and receiver portion 90 are engaged together with a "ball and joint" or swivel type of coupling that permits relative movement therebetween during at least some stages of assembly. In yet another form, bone attachment devices 22 may include one or more hooks to engage an adjacent bony structure such as a pedicle, lamina, spinous process, transverse process, or other bony structure suitable engaged with a spinal hook. For instance, a multi-axial laminar hook form of device 22 can be used in place of screw 82 and/or screw 84. In still other embodiments, device 22 can include a bone attachment structure in the form of a staple, bone plate, interbody fusion device, interbody spacer, spinal anchor, intravertebral fusion device, bone clamp, or other anchor.

In addition, rod 23 may be solid or hollow along some or all of its length and/or may be of homogenous or heterogeneous composition. Rod 23 can be rigid, or be flexible or include one or more flexible portions to permit at least limited spinal motion. Rod 23 may be substituted with any suitable spinal stabilization element positionable along the spinal column, including plates, tethers, wires, cables, cords, inflatable devices, expandable devices, and formed in place devices, for example.

The embodiment illustrated in FIG. 5 further includes two engaging members 100 and 101 structured to secure crosslink device 26 to bone screws 82 and 84, respectively, or other bone attachment devices. Engaging members 100 and 101 each include a longitudinal threaded stem 102, 102', respectively, opposite a head 104. Head 104 of each of engaging members 100, 101 includes a tool engagement cavity 106. Tool engagement cavity 106 may be, but is not limited to, a hex or allen wrench configuration. In alternative embodiments, tool engagement may be provided by a differently shaped structure for engagement by an appropriate assembly tool or may be absent. Indeed, in one alternative, engaging members 100 and 101 include a frangible, break-away portion which is engaged by a tool to rotate engaging members 100 and 101 into receiver portion 90 until a threshold torque level is reached, at which point the break-away portion fractures, separating from the remaining portions of engaging members 100, 101 at a pre-determined location.

Longitudinal threaded stem 102, 102' of each of engaging members 100, 101 passes through the respective aperture 60 of corresponding connectors 52 and 54 to engage threading 98 of the respective receiver portion 90. Once threaded therein and tightened, head 104 of each engaging member 100 and 101 bears against the corresponding connector 52 or 54 to secure the respective bridging members 28 and 40 to the respective receiver portions 90. It should be appreciated that head 104 is sized and shaped to contact connector 52 or 54 in a bearing relationship including where it forms a material boundary for the corresponding aperture 60. It should be further understood that connector 52 and 54 may rotate around the bone attachment device 22 until engaging members 100 and 101 are fully tightened to allow adjustment in the orientation of bridging members 28, 40.

FIG. 5 illustrates bone screw 82 having rod 23 positioned in receiver portion 90. In various embodiments of this application receiver portion 90 and rod 23 may differ in size in relation to one another and/or other components of system 20. As engaging member 100 is engaged in receiver portion 90, the end of threaded stem 102 can bear against rod 23 and force rod 23 against bottom portion 96 or other structure in receiver portion 90, securing rod 23 with crosslink device 26 and bone screw 82 in a rigid construct.

In FIG. 5 engaging member 101 is shown not completely engaged with receiver portion 90 of bone screw 84 in order to aid in the depiction of threading 98. However, stem 102' includes a length extending from head 104 such that its distal end stops at location 91 in receiver portion 90. At location 91, the distal end of stem 102' remains spaced from rod 23 in receiver portion 90. In this configuration, rod 23 is free to axially translate and move relative to bone screw 84 and cross-link device 26 while cross-link device 26 and bone screw 84 are rigidly coupled to one another. It is further contemplated the engaging members 100, 101 may be employed in either or both of bone screws 82, 84 or other bone attachment device 22.

In an alternative embodiment not shown, one or both of the connectors 52, 54 may include a structure that contacts the respective adjacent rod 23 when engaging member 101 with stem 102' is engaged to a bone attachment device 22. Accordingly, when engaging member 101 is tightened, it remains spaced from rod 23 in receiver portion 90, while connector 52, 54 includes a recess to receive receiver portion 90, or includes a structure extending distally therefrom toward rod 23 that contacts and securely engages rod 23 to receiver portion 90 of the bone attachment device.

It should be further understood that the embodiment illustrated in FIG. 5 shows the top or proximal end of 99 of the receiver portions 90 of bone screw 82 and bone screw 84 in different elevational planes. Crosslink device 26 is able to fittingly engage with proximal ends 99 of the receiver portions 90 or other structure of the bone attachment device 22 even if at different elevational planes and different angular orientations because connectors 52 and 54 pivot about fulcrum 64. While not shown, it should be understood that the elevational differences between the proximal ends 99 of bone attachment devices may be greater, smaller, or even the same in alternative embodiments.

Figure 6:
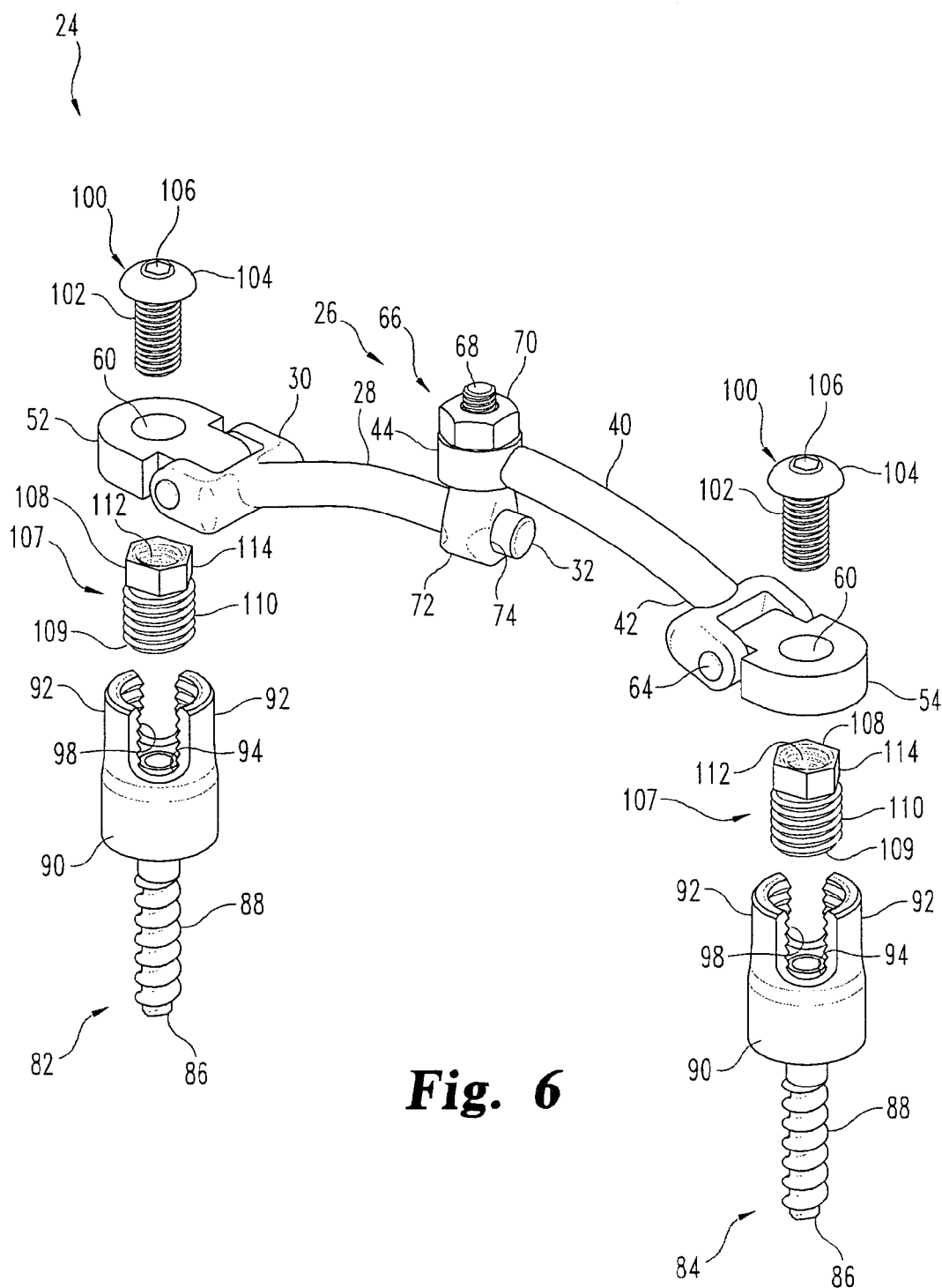
FIG. 6 is a perspective assembly view of the crosslink device relative with its connection to spinal implant components shown in exploded view.

FIG. 6 is a perspective assembly view of crosslink apparatus 24 wherein like numerals refer to like features previously described. In this embodiment a coupler 107 is utilized. Coupler 107 has first end 108 opposite a second end 109 and includes a longitudinal threaded stem 110 with an internally threaded portion 112. The first end 108 is further defined by a tool cooperation portion 114. Longitudinal threaded stem 110 of coupler 107 is structured to engage threading 98 when coupler 107 is rotated into receiver portion 90 of bone screws 82 and 84. While not shown, it is contemplated that the embodiment of FIG. 6 includes one or more rod(s) 23 through the respective receiver portions 90 of bone screws 82, 84. Rod(s) 23 is/are placed into rod receiving channel 94 and coupler 107 is engaged with threading 98 such that second end 109 bears against rod(s) 23 to create a rigid engagement between receiver portion 90 and rod 23.

Internally threaded portion 112 is structured to engage, for example, threaded stem 102 of engaging member 100 when engaging member 100 is inserted through aperture 60 of an adjacent one of the connectors 52 and 54. Once coupler 107 is tightened in receiver portion 90 and engaging member 100 is tightened in internally threaded portion 112, crosslink device 26 is locked in a rigid construct with bone screws 82 and 84 or other bone attachment devices 22. While bone screw 82 and bone screw 84 are both shown using coupler 107, it should be understood that in alternative embodiments coupler 107 may be absent from one or both of bone screw 82 and bone screw 84. It is further contemplated that coupler 107 may be used in alternative bone attachment devices 22 not illustrated in FIG. 6.

Figure 7:
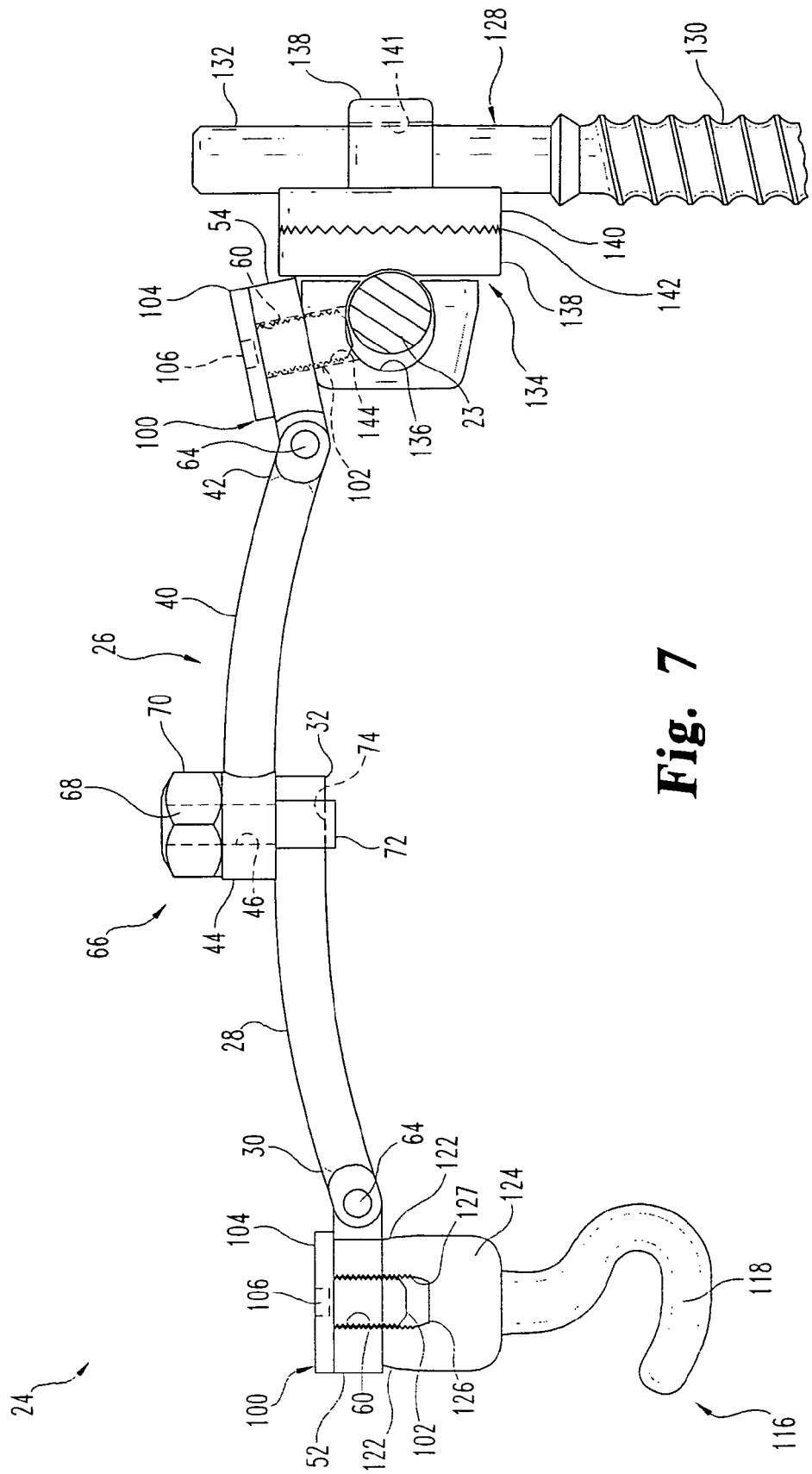
FIG. 7 is a side plan view of a crosslink device relative to other embodiment spinal implant components of the spinal fixation system of FIG. 1.

An alternative embodiment of crosslink apparatus 24 is shown in a side plan view in FIG. 7 where certain hidden features are shown in phantom and where like numerals refer to like features previously described. Connector 52 of crosslink device 26 is shown connected to a bone attachment device 22 in the form of a laminar hook 116. Laminar hook 116 includes a hook portion 118 structured to engage bone or a bony surface and a proximal head or receiver portion 124. Receiver portion 124 further includes a receiving channel 126 formed by a pair of upright arms 122 having internal threading 127 disposed therein. An engaging member, such as engaging member 100, can be passed through aperture 60 and engaged with threading 127 to create a rigid construct between connector 52 and laminar hook 116 and a rod or other elongate element positioned in receiving channel 126.

Opposite hood 116, another embodiment bone attachment device is shown. Connector 54 is shown connected to a bone attachment device 22 in the form of bone anchor 128 including a distal bone engaging portion 130 opposite a proximally extending post 132. Engaged about post 132 is a coupler clamp 134 including a receiver portion 136. Opposite the receiver portion 136 is a post engagement portion 138 including an aperture 141 through which post 132 extends. Coupler clamp 134 further includes a rod interface washer 138 and a post interface washer 140. Disposed on the side of washer 138 and washer 140 facing each other are a set of interdigitating teeth 142. Interdigitating teeth 142 are structured to allow lockable positioning of washer 138 and washer 140 such that the angular orientation of rod 23 relative to bone anchor 128 may be altered. However, once engaging member 100 is passed through aperture 60 and fully engaged with a threaded aperture 144 disposed near receiver portion 136, interdigitating teeth 142 become locked as rod 23 is forced to bias the washers 138, 140 into contact with one another. This occurs as threaded stem 102 presses against rod 23 forcing washers 138 and 140 together and pulling aperture 141 tight against post 132 to create a rigid construct between connector 54, rod 23, and bone anchor 128. Bone attachment devices 22 including bone anchor 128 and other forms are commercially available, for example, under the trade name TSRH-3D® spinal systems.

In alternative embodiments crosslink apparatus 24 is free from both engaging members 100, 101 and/or apertures 60 in connectors 52, 54. In these embodiments various means for connecting crosslink device 26 with bone attachment devices 22 are included. The means may include, but are not limited to, snap rings, nuts, pins, compression fits, snap fits, clamps, adhesives, and fusions. For example, engaging members 100, 101 are shown with externally threaded stems. Other embodiments contemplate engaging members 100, 101 with other structures for engaging receiver portion 32, including twist locks, snap fits, interference fits, slide-fits, clamps, expansion fits, and internally threaded stems, for example. As the connecting means change the corresponding structure of connector 52 and connector 54 will change. In embodiments including rod 23 the manner in which rod 23 is secured to one or both of bone attachment devices 22 will also change.

The components of cross-link apparatus 24 can be composed of medical grade stainless steel. Other embodiments may be composed of, but are not limited to, titanium, a titanium alloy or other metallic alloy, and/or a nonmetallic composition.

While the invention has been illustrated and described in detail in the drawings and foregoing description, the same is to be considered illustrative and not restrictive in character, it being understood that only selected embodiments have been shown and described and that all changes, equivalents, and modifications that come within the scope of the inventions described herein or defined by the following claims are desired to be protected. Any experiments, experimental examples, or experimental results provided herein are intended to be illustrative of the present invention and should not be construed to limit or restrict the invention scope. Further, any theory, mechanism of operation, proof, or finding stated herein is meant to further enhance understanding of the present invention and is not intended to limit the present invention in any way to such theory, mechanism of operation, proof, or finding. In reading the claims, words such as "a", "an", "at least on", and "at least a portion" are not intended to limit the claims to only one item unless specifically stated to the contrary. Further, when the language "at least a portion" and/or "a portion" is used, the claims may include a portion and/or the entire item unless specifically stated to the contrary.

What is claimed is:

1. An apparatus, comprising:
two bone attachment devices structured to anchor to bone, each of the bone attachment devices including a distal bone engaging portion and a proximal end opposite the distal bone engaging portion;
a crosslink device structured to interconnect the two bone attachments devices and adjustably span a distance separating the two bone attachment devices, the crosslink device including:
a first member extending along a first longitudinal axis between and including a first end portion and an opposite first connector including a body structured to engage a first one of the bone attachment devices and the first connector being pivotal relative to the first member, wherein one of the first member and the first connector includes a branch and the other of the first member and the first connector includes a socket, wherein the socket includes an opening extending therethrough that extends along a pivot axis in a transverse orientation to the first longitudinal axis, the branch and socket being pivotally coupled to one another and structured so that the first connector pivots relative to the first member around the pivot axis in a proximal direction away and in a distal direction toward the proximal end of the first bone attachment device to align the first connector with the proximal end of the first bone attachment device;
a second member extending along a second longitudinal axis and including a second end portion and an opposite second connector including a body structured to engage a second one of the bone attachment devices and the second connector being pivotal relative to the second member;
an interconnection device positioned between the first end portion and the second end portion to interconnect the first member and the second member together, wherein the first member is rotatable in the interconnection device to rotate the first connector around the longitudinal axis to align the first connector with the proximal end of the first bone attachment device; and
two engaging members, a first one of the engaging members being structured to engage the first connector and the first bone attachment device when the first connector is aligned with the first one of the bone attachment devices to secure the first member thereto, and a second one of the engaging members being structured to engage the second connector and the second bone attachment device when the second connector is aligned with the second one of the bone attachment devices to secure the second member thereto, wherein at least one of the bone attachment devices includes a receiver portion at the proximal end of the bone attachment device and an elongate spinal stabilization element extending through the receiver portion in a transverse orientation to the crosslink device, and at least one of the engaging members includes a head at a proximal end thereof and a threaded stem extending from the head that is threadingly engaged in the receiver portion, wherein the head contacts the respective connector to rigidly engage crosslink device to the receiver portion while a distal end of the threaded stem is spaced from the elongate spinal stabilization element in the receiver portion so that the elongate spinal stabilization element is free to axially translate and rotate relative to the at least one bone attachment device when the crosslink device is rigidly engaged to the at least one bone attachment device.

2. The apparatus of claim 1 wherein the receiver portion includes an internal threading and the threaded stem threadingly engages the internal threading along the receiver portion.

3. The apparatus of claim 1, wherein each of the two bone attachment devices includes a receiver portion at the proximal end thereof and an elongate spinal stabilization element extending through the receiver portion thereof in a transverse orientation to the crosslink device, and each of the two engaging members includes a head at a proximal end thereof and a threaded stem extending from the head that is threadingly engaged in the receiver portion of the respective bone attachment device, wherein the heads contact the respective connector to rigidly engage crosslink device to the receiver portions while a distal end of the threaded stem is spaced from the respective elongate spinal stabilization element in the receiver portion so that the elongate spinal stabilization elements are free to axially translate and rotate relative to the two bone attachment devices when the crosslink device is rigidly engaged to the bone attachment devices.

4. The apparatus of claim 1 wherein the bone attachment devices each include said bone engaging portion in the form of a bone screw and a proximal receiver portion that is pivotal relative to the bone screw.

5. The apparatus of claim 1, wherein:
one of the second member and the second connector includes a branch and the other of the second member and the second connector includes a socket, the branch and socket being pivotally coupled to one another.

6. The apparatus of claim 5 wherein the socket of the one of the second member and the second connector includes an aperture therethrough, the aperture thereof being transverse to the second longitudinal axis of the second member.

7. The apparatus of claim 6 wherein each of the first connector and the second connector includes a longitudinal axis and wherein each of the branches includes an aperture therethrough, the aperture being transverse to the longitudinal axis of an adjacent one of the first connector and the second connector.

8. The apparatus of claim 7 further comprising a first pin and a second pin each structured to extend through the aperture of a respective one of the first connector and the second connector to couple the branch to the socket and pivotally secure the respective first and second connector with the respective first and second member.

9. The apparatus of claim 8 wherein the first pin and the second pin each permits pivotal rotation of the respective one of the first and second connectors relative to the respective first and second member.

10. The apparatus of claim 1 wherein at least one of the two bone attachment devices includes a post extending proximally from the bone engaging portion, and a coupler clampingly engaged about the post.

11. The apparatus of claim 1 wherein the interconnection device further includes a fastener structured to fix the second member relative to the stem when the fastener is engaged to the stem.

12. The apparatus of claim 1 wherein each of the bone attachment devices includes a receiver portion at a proximal end thereof and the first connector and the second connector each define an aperture extending therethrough that is aligned with the receiver portion of the respective bone attachment device.

13. The apparatus of claim 12 wherein each of the receiver portions of the bone attachment devices includes a channel and an elongate spinal stabilization element extending through the channel in a transverse orientation to the crosslink device, and each of the two engaging members extends through a respective one of the apertures and engages the aligned receiver portion to secure the connector to the receiver portion.

14. The apparatus of claim 13 wherein the other of the receiver portions further comprises a coupler therein, the coupler defining a body with an external portion including threads for engaging the channel and an interior threaded portion for threadingly engaging the respective engaging member engaged to the receiver portion.

15. The apparatus of claim 12 wherein the other of the receiver portions includes a coupler clamp engaged thereto, the coupler clamp including a threaded aperture and wherein respective engaging member includes a threaded fastener structured to extend through the aperture of the respective connector aligned with the other of the receiver portions to engage the threaded aperture of the coupler clamp and couple the respective connector to the other of the receiver portions.

16. The apparatus of claim 1 wherein the first member and the second member adjustably attach to the two bone attachment devices over a range of angular orientations of the respective first and second member relative to the respective bone attachment device.

* * * * *

UNITED STATES PATENT AND TRADEMARK OFFICE
CERTIFICATE OF CORRECTION

| | |
|---|---|
| PATENT NO. | : 7,837,714 B2 |
| APPLICATION NO. | : 11/401732 |
| DATED | : November 23, 2010 |
| INVENTOR(S) | : Drewry et al. |

It is certified that error appears in the above-identified patent and that said Letters Patent is hereby corrected as shown below:

On the Face Page, in Field (56), under "U.S. PATENT DOCUMENTS", in Column 2, Line 11, delete "Choi et al." and insert -- Lee et al. --, therefor.

In Column 10, Line 65, in Claim 11, after "to fix the", insert -- first member in the passageway and to fix the --, therefor.

Signed and Sealed this
Twenty-second Day of November, 2011

David J. Kappos
*Director of the United States Patent and Trademark Office*